(12) United States Patent
Puskas et al.

(10) Patent No.: US 8,147,512 B1
(45) Date of Patent: Apr. 3, 2012

(54) DUAL CLOSING GUIDE FOR A SURGICAL INSTRUMENT

(75) Inventors: John Puskas, Atlanta, GA (US); Gaylord Kube, Oakdale, MN (US)

(73) Assignees: Scanlan International, Inc., St. Paul, MN (US); Emory University, Atlanta, GA (US)

( * ) Notice: Subject to any disclaimer, the term of this patent is extended or adjusted under 35 U.S.C. 154(b) by 755 days.

(21) Appl. No.: 12/134,842

(22) Filed: Jun. 6, 2008

Related U.S. Application Data

(60) Provisional application No. 60/942,385, filed on Jun. 6, 2007.

(51) Int. Cl.
*A61B 17/50* (2006.01)

(52) U.S. Cl. ...................................... 606/210

(58) Field of Classification Search .................... 606/72, 606/139–142, 169–174, 184, 185, 205–210, 606/213

See application file for complete search history.

(56) References Cited

U.S. PATENT DOCUMENTS

| | | | | |
|---|---|---|---|---|
| 3,392,727 | A * | 7/1968 | Hanlon | 606/210 |
| 4,793,349 | A * | 12/1988 | Weinrib | 606/148 |
| 2005/0125033 | A1* | 6/2005 | McNally-Heintzelman et al. | 606/213 |

\* cited by examiner

*Primary Examiner* — Kevin T Truong
(74) *Attorney, Agent, or Firm* — Faegre Baker Daniels LLP

(57) ABSTRACT

A hand-operated surgical instrument with sequentially engaged tip closing guides. The instrument includes first and second arms having tips that close during a closure operation. A slotted tip closure guide on the arms engages first during the closure operation. A pin closure guide on the arms between the slotted closure guide and the tips engages during the closure operation after the engagement of the slotted closure guide. The sequential engagement of the guides provides precise approximation of the instrument tips and prevents "scissoring" of the tips.

20 Claims, 1 Drawing Sheet

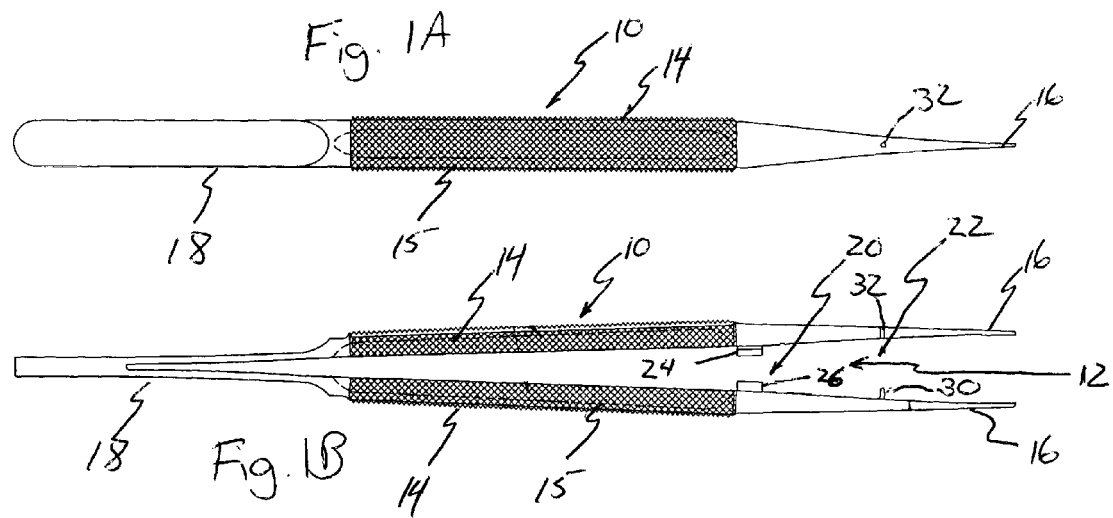
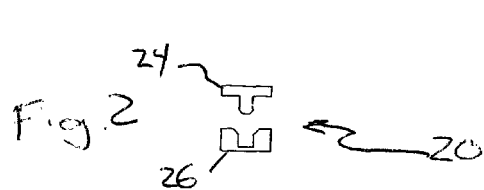
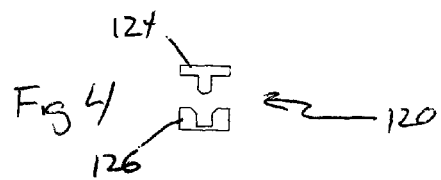
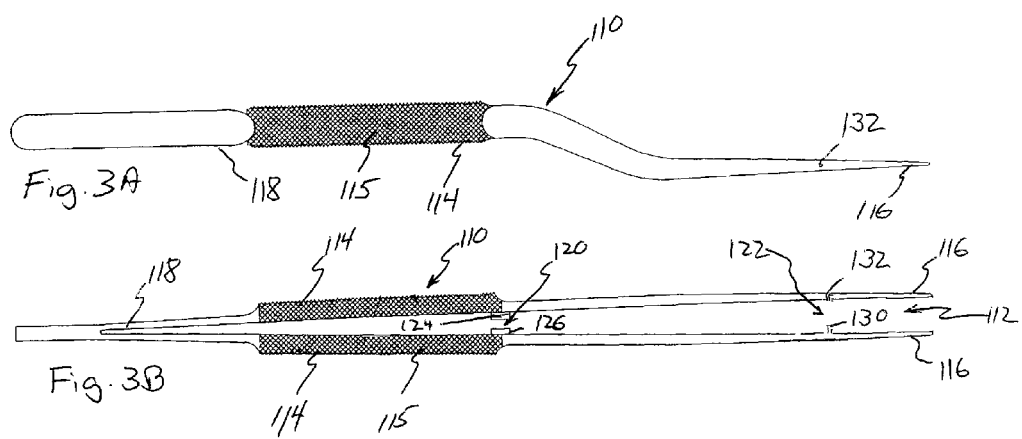

DUAL CLOSING GUIDE FOR A SURGICAL INSTRUMENT

REFERENCE TO RELATED APPLICATION

This application claims the benefit of U.S. Provisional Application Ser. No. 60/942,385, filed on Jun. 6, 2007 and entitled Dual Closing Guide For A Surgical Instrument, which is incorporated herein by reference in its entirety.

FIELD OF THE INVENTION

The invention relates generally to surgical instruments. In particular, the invention is a closing guide for surgical instruments.

BACKGROUND OF THE INVENTION

The handling of delicate tissue during surgical procedures is generally performed utilizing precisely designed surgical instruments. In particular, a surgical forceps (tweezers style), or "pick-ups" is commonly used as it is designed to provide for precisely grasping tissue between the tips. The tips are sometimes very narrow (1 mm or less) and can be on a straight or bayonet style forceps as long as 180 mm or longer. The fine tips, especially when on a long forceps, may inadvertently cross or "scissor" when force is applied to the handles in an uneven manner. Manipulation of tissue between the tips of the forceps may also cause scissoring. This action may lead to shearing of the tissue and reduces the accuracy and delicate handling of the tissue that is necessary to assure successful surgical manipulation of the tissue.

To reduce or minimize the cross over of the tips, a guide pin is incorporated into the design of some surgical forceps. The guide pin design includes a straight or slightly tapered pin located approximately ¼ to ⅓ of the distance from the tip. The guide pin mates with a thru hole opposite the pin. As the forceps tips are moved together during surgical manipulation the pin enters the receiving hole guiding the tips together and reducing the opportunity for the tips to cross. Although this is sometimes effective, it has other undesired affects on the performance of the forceps. The pin contacting the hole may transfer the sensation through the shaft affecting the tactile feedback of the forceps. The guide pin may also, through handling and processing, become deflected from its perpendicular position and interfere with the proper closing of the forceps. Even when the pin is not bent, it may catch on the edge of the thru hole when the forceps are "scissored". While this will prevent crossing of the tips, it also prevents closure of the forceps and does so with an unpleasing abruptness.

There remains, therefore, a continuing need for improved structures to enable the closure of surgical and other instruments.

SUMMARY OF THE INVENTION

The present invention is an improved closing guide for surgical and other instruments. The guide can prevent crossing of the tips without interfering with the tactile feel of the instrument.

One embodiment of the invention includes first and second arms having tips, and first and second closing guides including structures on the first and second arms. The structures of the first closing guide engage one another when the arms are moved to a first closing position from an open position, and guide the tips to closure. The structures of second closing guide are between the first closing guide and the tips, engage one another when the arms are moved to a second closing position beyond the first closing position, and guide the tips to closure. In another embodiment of the invention the first closing guide is a slotted guide and the second closing guide is a pin guide.

BRIEF DESCRIPTION OF THE DRAWINGS

FIGS. 1A and 1B are top and side views, respectively, of a round handle surgical forceps having a dual closing guide in accordance with one embodiment of the invention.

FIG. 2 is a detailed view of the slotted guide of the forceps shown in FIGS. 1A and 1B.

FIGS. 3A and 3B are top and side views, respectively, of a bayonet handle surgical forceps having a dual closing guide in accordance with another embodiment of the invention.

FIG. 4 is a detailed view of the slotted guide of the forceps shown in FIGS. 3A and 3B.

DETAILED DESCRIPTION OF THE PREFERRED EMBODIMENTS

A surgical forceps 10 having a dual closing guide 12 in accordance with one embodiment of the invention is illustrated in FIGS. 1A and 1B. The forceps 10 includes a pair of arms 14 having handles 15 and tips 16 at their distal ends. The proximal ends 18 of the arms 14 are joined together in such a manner that the arms are biased to a position with the tips 16 open as shown in FIG. 1B. During use of the forceps 10 to grasp tissue, a surgeon can hold the arms 14 at handles 15 and squeeze the arms together against the bias force during a closing operation, thereby closing the tips 16 to grasp the tissue. In the embodiment shown in FIGS. 1A and 1B handles 15 are round and have knurled surfaces. Other embodiments of the invention have handles 15 with different shapes and surface structure.

The dual closing guide 12 includes a slotted closing guide 20 (i.e., a first closing guide) and a pin closing guide 22 (i.e., a second closing guide) between the slotted guide and the forceps tips 16. As perhaps best shown in FIGS. 1B and 2, slotted guide 20 includes a male member 24 (i.e., a guide structure) on one arm 14 and a female member 26 (i.e., a guide structure) on the other arm 14. Male member 24 mates with the slot of female member 26 and can have a rectangular or semi-circular cross section (a rectangular member is shown in FIGS. 1B and 2) and be straight or tapered throughout its height. Female member 26 has a complimentary rectangular or circular cross sectional shape, with a bisecting relief to provide for precise placement without interference of the male member 24. In the embodiment shown in FIG. 2, the slot in the female member 26 has tapered edges that open toward the male member 24 to provide a gradual approximation of the tips 16 moving into proper alignment. The surfaces of the male member 24 and female member 26 can be sufficiently smooth to provide minimal friction and to minimize sensations from contact with one another. The slotted guide 20 thereby provides increasing guide tolerances during the closure operation (i.e., with continuing closure the slotted guide causes the tips 16 to be increasing aligned in position).

Pin closing guide 22 includes a pin 30 (i.e., a guide structure) on one of the arms 14, and a hole 32 (i.e., a guide structure) on the other arm 14. In one embodiment the pin 30 is a round, tapered member and is located on the same arm 14 that has as the female member 26 of the slotted guide 20. The hole 32 is sized to mate with pin 30, and can have a funnel-shaped opening tapering to a straight channel to receive the pin. The surfaces of the pin 30 and hole 32 are preferably sufficiently smooth to provide minimal friction and to minimize sensations from contact with each other.

In the embodiment shown in FIGS. 1A and 1B, the slotted guide 20 is spaced from the tips 16 by a distance equal to about one-third of the length of the arms 14, and the pin guide 22 is positioned approximately midway between the slotted guide and the tips. In other embodiments the slotted guide 20 and pin guide 22 are positioned at other locations along the forceps arms 14.

The slotted closing guide 20 and pin closing guide 22 are configured to engage in sequence during the closing operation of the forceps 10. When the arms 14 and tips 16 are in the open position shown in FIG. 1B, neither the slotted guide nor the pin guide is engaged. Through a first stage of the tip closure operation both the slotted guide 20 and the pin guide 22 remain disengaged. At an end of the first stage of the closure operation (i.e, at a first closing position) the slotted guide 20 will engage (i.e., the male member 24 and female member 26 will mate). The tip closure operation then continues through a second stage with only the slotted guide 20 is engaged. Although the pin guide 22 is still disengaged and the tips 16 are still open during the second stage of the closure operation, the slotted guide 20 provides a first or coarse guide function, guiding the pin guide toward its engaged position and the tips toward their proper closed position. The increasing tolerance features of the slotted guide 20 cause the pin guide 22 and tips 16 to increasingly align throughout the second stage of the closure operation (i.e., at a second closing position). At the end of the second stage of the tip closure operation the pin guide 22 will engage (i.e., the pin 30 and hole 32 will mate). The closure operation then continues through a third stage with both the slotted guide 20 and the pin guide 22 engaged. The engaged pin guide 22 provides a second or fine guide function, guiding the tips 16 to their proper closed position without crossing.

The configuration of the slotted closing guide 20 and pin closing guide 22 to enable the sequential closing operation of the forceps 10 can be accomplished in several ways. For example, the size and position of the guides 20 and 22 can be selected to provide the desired closing sequence and to cause the guides to engage at desired positions in the closing operation. The nature of the arms 14 (i.e., whether they are straight or bowed) is also a factor affecting the configuration of the guides 20 and 22 (i.e. the guide structures may have to be longer if located on bowed portions of the arms). Although the female member 26 of slotted guide 20 extends from the arm 14 on which it is mounted, this and other guide structures can alternatively be formed in the arm (e.g., a trench recessed in the arm).

The dual closing guide 20 provides precise, accurate closing of the forceps tips 16 without interference with or adverse affect on the tactile feedback. The combination and cooperation of the several guides 20, 22 provide for the progressive approximation of both guides, assuring that the tips 16 align correctly and precisely to grasp the tissue with delicate precision. The slotted guide 20 facilitates the correct alignment of the pin guide and enables the pin guide 22 to engage without a "catch." The pin guide 22 then ensures correct alignment of the forceps tips 16 and prevents scissoring.

The guides 20 and 22 can be structured to provide increasingly precise guide alignment functions with continuing engagement of the guides. The tapered surfaces on the guides 20 and 22, for example, enable the guides to initially engage even if the arms 14 and tips 16 are not fully aligned. With continuing closure after initial engagement the guides effectively force the arms 14 and tips 16 into increasingly accurate alignment. The increasing alignment structures on the guides 20 and 22 can be configured to continue from the initial engagement of the slotted guide 20, through the initial engagement of pin guide 22 and to the closure of the tips 16. The guides 20 and 22 therefore provide "forgiveness" of potentially stressed or bent instruments, as well as overcoming "scissoring" forces applied to the arms 14 and tips 16 by tissue engaged by the tips.

FIGS. 3A, 3B and 4 illustrate a bayonet handle forceps 110 in accordance with another embodiment of the invention. As shown in FIG. 1A, the handle 14 is offset from the tips 16. Other than this difference, forceps 110 can be substantially the same as or similar to forceps 10 described above, and similar features are identified with similar reference numbers. In particular, slotted closing guide 220 and pin closing guide 222 cooperate during the closing operation of the forceps 110 in the same manner as guides 20 and 22 of forceps 10 described above.

Although the present invention has been described with reference to preferred embodiments, those skilled in the art will recognize that changes can be made in form and detail without departing from the spirit and scope of the invention. In particular, although described in connection with specific types of forceps, the dual closing guide can be incorporated into other surgical instruments having two or more arms with tips that close, including for example other forceps types, clamps, clip appliers, bipolar cautery instruments, electrosurgery forceps and other tweezer-like instruments. The dual closing guide can also be incorporated into non-medical instruments used in other applications. The invention can also include more than two sequential guides.

What is claimed is:

1. An instrument, including:
   first and second arms having tips, wherein the arms are movable back and forth between open and closed positions during operation of the instrument;
   a first closing guide including structures on the first and second arms, wherein the structures of the first closing guide engage one another when the arms are moved to a first closing position from the open position, and continue to engage and continue to move with respect to one another as the arms are moved to a second closing position beyond the first closing position to guide the tips to closure; and
   a second closing guide including structures on the first and second arms between the first closing guide and the tips, wherein the structures of the second closing guide engage one another when the arms are moved to the second closing position, and continue to engage and continue to move with respect to one another as the arms are moved beyond the second closing position to guide the tips to closure, wherein the structures of the second closing guide are disengaged until the arms are moved to the second closing position.

2. The instrument of claim 1 wherein the first closing guide includes a slotted guide.

3. The instrument of claim 2 wherein the slotted guide includes increasing alignment structure to provide increasing tip alignment with continuing closure of the arms.

4. The instrument of claim 3 wherein the increasing alignment structure includes a tapered surface.

5. The instrument of claim 2 wherein the slotted guide includes a male member on the first arm and a female member on the second arm.

6. The instrument of claim 5 wherein the pin guide includes a hole on the first arm and a pin on the second arm.

7. The instrument of claim 6 wherein the pin guide includes increasing alignment structure to provide increasing tip alignment with continuing closure of the arms.

8. The instrument of claim 1 wherein the second closing guide includes a pin guide.

9. The instrument of claim 1 wherein:
the first closing guide includes a slotted guide; and
the second closing guide includes a pin guide.

10. The instrument of claim 9 wherein:
the slotted guide includes:
 a male member on the first arm; and
 a female member on the second arm; and
the pin guide includes:
 a hole on the first arm; and
 a pin on the second arm.

11. The instrument of claim 9 wherein the instrument is a hand-operated surgical instrument and the first and second arms are biased to the open position.

12. The surgical instrument of claim 1 wherein the first and second arms are biased to the open position.

13. A hand-operated surgical instrument, including:
first and second arms having tips, where in the arms are movable back and forth between open and closed positions during operation of the instrument, and wherein the arms and tips move through sequential, first, second and third stages of closure as the arms move from the open position to a first closing position, to a second closing position after the first closing position, and to a closed position after the second closing position during a closure operation;
a first tip closure guide on the arms that is disengaged during the first stage of the closure operation as the arms move from the open position to the first closing position, and that movably engages and remains movably engaged during the second and third stages of the closure operation; and
a second tip closure guide on the arms between the first tip closure guide and the tips, that is disengaged during the first and second stages of the closure operation and that movably engages and remains movably engaged during the third stage of the closure operation after the engagement of the first tip closure guide.

14. The surgical instrument of claim 13 wherein the first tip closure guide includes increasing alignment structure to provide increasing tip alignment during the closure operation.

15. The surgical instrument of claim 14 wherein the first tip closure guide is a slotted guide.

16. The surgical instrument of claim 15 wherein the second tip closure guide is a pin guide.

17. The surgical instrument of claim 13 wherein the second tip closure guide is a pin guide.

18. The surgical instrument of claim 13 wherein the first tip closure guide is a slotted guide.

19. The surgical instrument of claim 13 wherein the second tip closure guide includes increasing alignment structure to provide increasing tip alignment during the closure operation.

20. The surgical instrument of claim 13 wherein the first and second arms are biased to the open position.

* * * * *